United States Patent

Mori et al.

[11] Patent Number: 5,922,882
[45] Date of Patent: Jul. 13, 1999

[54] BISBENZOTRIAZOLYLPHENOL COMPOUND

[75] Inventors: Koji Mori; Emiko Daimon, both of Itano-gun; Koji Ishida, Tondabayashi; Shinji Nakano, Itano-gun; Takashi Ogawa, Naruto; Kazuhiro Kawano, Tokushima; Mitsuo Akada, Itano-gun, all of Japan

[73] Assignee: Otsuka Kagaku Kabushiki Kaisha, Osaka, Japan

[21] Appl. No.: 08/973,222

[22] PCT Filed: Mar. 19, 1997

[86] PCT No.: PCT/JP97/00940

§ 371 Date: Nov. 26, 1997

§ 102(e) Date: Nov. 26, 1997

[87] PCT Pub. No.: WO97/35847

PCT Pub. Date: Feb. 10, 1997

[30] Foreign Application Priority Data

Mar. 28, 1996 [JP] Japan .................. 8-074191
Mar. 11, 1997 [JP] Japan .................. 9-056190

[51] Int. Cl.[6] .................................. C07D 249/18
[52] U.S. Cl. .................... 548/260; 548/255; 548/257
[58] Field of Search .................... 548/255, 257, 548/260

[56] References Cited

FOREIGN PATENT DOCUMENTS 50-161538  12/1975  Japan .

Primary Examiner—Johann Richter
Assistant Examiner—Ebenezer Sackey
Attorney, Agent, or Firm—Knobbe, Martens, Olson & Bear LLP

[57] ABSTRACT

An object of the present invention is to provide a novel bisbenzotriazolylphenol compound having a UV absorving effect. The bisbenzotriazolylphenol compound of the invention is represented by the formula

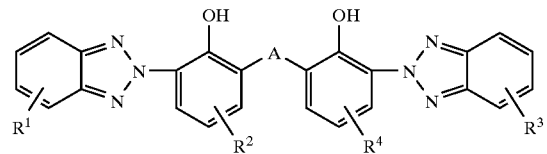

wherein A is a direct bond or represents a $C_{1-6}$ alkylene group, a —$C(CH_3)_2$— group, a —$C(C_2H_5)(CH_3)$— group, a —O— group or a —NH— group, $R^1$ and $R^3$ are the same or different and each represent a hydrogen atom, a $C_{1-4}$ alkyl group, an aryl group, a $C_{1-4}$ alkoxy group or a halogen atom, and $R^2$ and $R^4$ are the same or different and each represent a hydroxyl group or a $C_{1-12}$ straight- or branched-chain hydroxyalkyl group.

6 Claims, No Drawings

BISBENZOTRIAZOLYLPHENOL COMPOUND

This application is a 371 of PCT/JP97/00940 filed Mar. 19, 1997.

FIELD OF THE INVENTION

The present invention relates to novel bisbenzotriazolylphenol compounds and copolymers containing the compound as a copolymerization component.

PRIOR ART

2-Hydroxyphenylbenzotriazole compounds are known as UV absorbers useful for protecting plastics from UV rays. However, most of the known UV absorbers are low-molecular compounds which cause a number of problems. For example, conventional benzotriazole-based UV absorbers have high vapor pressures because of their low molecular weights, and are known to transpire when blended with a resin and subjected to a molding process, polluting working environment and staining the mold. Further, conventional UV absorbers are of addition type and used as merely mixed with the base resin. Therefore, they tend to bleed out of the obtained molded article or coating film with the lapse of time, or are washed out by rain or detergent-containing water in using environment, failing to impart light stability to the product for a long period.

Some methods have been proposed in which the conventional low-molecular weight compounds used as UV absorbers are converted into high-molecular compounds to solve the above problems.

For example, Japanese Examined Patent Publiation No. 25036/1963 and Japanese Unexamined Patent Publications Nos. 51181/1985 and 112062/1986 disclose high-molecular UV absorbers obtained from polymerizable benzotriazole compounds. However, these compounds can be used only in the form of copolymers with addition polymerizable monomers, and cannot be used for polymers produced by polycondensation.

Japanese Unexamined Patent Publications Nos. 188581/1990 and 200788/1991 disclose condensation polymerizable benzotriazole compounds having a plurality of carboxyl groups in the molecule. However, as apparent from their structures, these compounds, although usable in the production of polyesters or polyamides, cannot be employed in the production of polycarbonates or polyurethanes which are particularly susceptible to deterioration by UV rays.

Further, Japanese Examined Patent Publication No. 20913/1992 discloses benzotriazole and bisbenzotriazole compounds having a plurality of hydroxyalkyl groups. However, since the hydroxyalkyl groups are introduced into the compounds through ester bonds, these compounds undergo hydrolysis or ester exchange when used as comonomers in polycondensation. These reactions can cause troubles especially in polymerization under alkaline conditions or in polyester production requiring high temperature polymerization. In addition, carboxyl- or ester-containing benzotriazole compounds are produced as by-products and act as stoppers, preventing the rise in the polymerization degree.

Further, Japanese Examined Patent Publication No. 39180/1980 discloses dimerized benzotriazole compounds, and Japanese Unexamined Patent Publication No. 39326/1991 teaches weather-resistant polycarbonates prepared using the dimerized compound as a copolymerization monomer. However, when the dimerized compound is used as the copolymerization monomer of the polycarbonate, phenolic hydroxyl groups, which are essential functional groups for imparting UV absorptivity, inevitably participate in the copolymerization and are lost. As a result, the obtained polycarbonate has insufficient light resistance.

DISCLOSURE OF THE INVENTION

An object of the present invention is to provide a novel bisbenzotriazolylphenol compound useful as an UV absorber, the compound having good UV absorptivity, very low vapor pressure and high heat stability.

Another object of the present invention is to provide a bisbenzotriazolylphenol compound which does not transpire even when blended with a resin requiring high molding temperature (e.g., engineering plastics) and subjected to a melt-molding process.

A further object of the present invention is to provide a copolymer comprising the bisbenzotriazolylphenol compound as a copolymerization component.

Other features of the present invention will be apparent from the following description.

The bisbenzotriazolylphenol compound of the invention is a novel compound which has not been disclosed in any literature. The compound is represented by the formula (1)

(1)

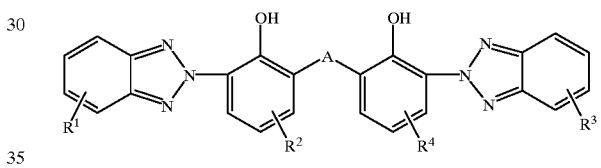

wherein A is a direct bond or represents a $C_{1-6}$ alkylene group, a —C(CH$_3$)$_2$— group, a —C(C$_2$H$_5$)(CH$_3$)— group, a —O— group or a —NH— group, $R^1$ and $R^3$ are the same or different and each represent a hydrogen atom, a $C_{1-4}$ alkyl group, an aryl group, a $C_{1-4}$ alkoxy group or a halogen atom, and $R^2$ and $R^4$ are the same or different and each represent a hydroxyl group or a $C_{1-12}$ straight- or branched-chain hydroxylalkyl group.

The bisbenzotriazolylphenol compound represented by the formula (1) is useful, for example, as a UV absorber. The bisbenzotriazolylphenol compound of the invention exhibits good UV absorptivity, very low vapor pressure and high heat stability, and is useful as an addition type UV absorber.

The bisbenzotriazolylphenol compound of the invention does not transpire even when blended with a resin requiring high molding temperature (e.g., engineering plastics) and subjected to a melt-molding process.

The bisbenzotriazolylphenol compound of the invention which contains two hydroxylalkyl groups in the molecule has various features that are not found in conventional UV absorbers. The features include reactivity with phosgene which enables introduction of the compound into the main chain of polycarbonates, reactivity with dicarboxylic acids or dicarboxylic acid esters which enables introduction of the compound into the main chain of polyesters, and reactivity with isocyanates which enables introduction of the compound into the main chain of urethane resins.

The bisbenzotriazolylphenol compound of the invention is copolymerizable with condensation polymerizable monomers. Accordingly, the UV absorber unit can be introduced at almost any ratio into the main chain or side chain of polymers obtained by polycondensation (such as polycarbonates, polyesters or polyurethanes). The resulting UV absorptive copolymer does not lose its UV absorptivity nor transpire when heated in the molding process. Moreover, the UV absorber does not bleed out from the molded product, and thus can impart to the product sufficient weather resistance for a long period.

When the bisbenzotriazolylphenol compound of the invention having a plurality of highly reactive hydroxyalkyl groups in the molecule is reacted with a comonomer copolymerizable therewith to obtain a polymer, the UV absorber unit can be introduced into the main chain of the polymer at any ratio without losing phenolic hydroxyl groups. Accordingly, the obtained copolymer maintains 100% of the excellent UV absorptivity of the benzotriazolylphenol compound.

Further, the bisbenzotriazolylphenol compound of the invention has very low vapor pressure and remarkably high decomposition temperature of 350° C. or higher. Thus, the compound, even when subjected to high temperature polycondensation, does not transpire or decompose during the reaction, giving a weather resistant polycondensation polymer with a desired molecular weight in a high yield.

The groups shown in the formula (1) are specifically described below.

The $C_{1-6}$ alkylene group is, for example, methylene, ethylene, trimethylene, 2-methyltrimethylene, 2,2-dimethyltrimethylene, 1-methyltrimethylene, methylmethylene, ethylmethylene, tetramethylene, pentamethylene, hexamethylene or the like.

The $C_{1-4}$ alkyl group is, for example, methyl, ethyl, propyl, isopropyl, butyl, isobutyl, tert-butyl or the like.

The aryl group is, for example, phenyl, naphthyl or like group which may have a $C_{1-4}$ alkyl group, a $C_{1-4}$ alkoxy group, a halogen atom or the like on the phenyl ring.

The $C_{1-4}$ alkoxy group is, for example, methoxy, ethoxy, propoxy, isopropoxy, butoxy, tert-butoxy or the like.

The halogen atom is fluorine, chlorine, bromine or iodine.

The $C_{1-12}$ straight- or branched-chain hydroxyalkyl group is, for example, a $C_{1-12}$ straight- or branched-chain alkyl group having 1 to 3 hydroxyl groups, such as hydroxymethyl, 2-hydroxyethyl, 1-hydroxyethyl, 3-hydroxypropyl, 2,3-dihydroxypropyl, 4-hydroxybutyl, 1,1-dimethyl-2-hydroxyethyl, 5,5,4-trihydroxypentyl, 5-hydroxypentyl, 6-hydroxyhexyl, 1-hydroxyisopropyl, 2-methyl-3-hydroxypropyl, 7-hydroxyheptyl, 8-hydroxyoctyl, 9-hydroxynonyl, 10-hydroxydecyl, 11-hydroxyundecyl or 12-hydroxydodecyl.

Among the compounds of the invention represented by the formula (1), preferred are those in which $R^2$ and $R^4$ are both $C_{1-12}$ straight- or branched-chain hydroxyalkyl groups. Among such compounds, especially preferred are those in which A is a methylene group.

Specific examples of the bisbenzotriazolyl-phenol compound of the invention are given below.

2,2'-Methylenebis[6-(2H-benzotriazole-2-yl)-2,4-dihydroxybenzene]

2,2'-Methylenebis[6-(2H-benzotriazole-2-yl)-4-(hydroxymethyl)phenol]

2,2'-Methylenebis[6-(2H-benzotriazole-2-yl)-4-(2-hydroxyethyl)phenol]

2,2'-Methylenebis[6-(5-chloro-2H-benzotriazole-2-yl)-4-(2-hydroxyethyl)phenol]

2,2'-Methylenebis[6-(5-bromo-2H-benzotriazole-2-yl)-4-(2-hydroxyethyl)phenol]

2,2'-Methylenebis[6-(2H-benzotriazole-2-yl)-4-(3-hydroxypropyl)phenol]

2,2'-Methylenebis[6-(5-chloro-2H-benzotriazole-2-yl)-4-(3-hydroxypropyl)phenol]

2,2'-Methylenebis[6-(5-bromo-2H-benzotriazole-2-yl)-4-(3-hydroxypropyl)phenol]

2,2'-Methylenebis[6-(2H-benzotriazole)-2-yl)-4-(2-hydroxypropyl)phenol]

2,2'-Methylenebis[6-(5-chloro-2H-benzotriazole-2-yl)-4-(2-hydroxypropyl)phenol]

2,2'-Methylenebis[6-(5-bromo-2H-benzotriazole-2-yl)-4-(2-hydroxypropyl)phenol]

2,2'-Methylenebis[6-(2H-benzotriazole-2-yl)-4-(4-hydroxybutyl)phenol]

2,2'-Methylenebis[6-(5-chloro-2H-benzotriazole-2-yl)-4-(4-hydroxybutyl)phenol]

2,2'-Methylenebis[6-(5-bromo-2H-benzotriazole-2-yl)-4-(4-hydroxybutyl)phenol]

3,3-{2,2'-Bis[6-(2H-benzotrizole-2-yl)-1-hydroxy-4-(2-hydroxyethyl)phenyl]}propane 2,2-{2,2'-Bis[6-(2H-benzotriazole-2-yl)-1-hydroxy-4-(2-hydroxyethyl)phenyl]}butane 2,2'-Bis[6-(2H-benzotriazole-2-yl)-4-(2-hydroxyethyl)phenol]ether 2,2'-Bis[6-(2H-benzotriazole-2-yl)-4-(2-hydroxyethyl)phenol]amine 2,2'-Bis[6-(2H-benzotriazole-2-yl)-4-(2-hydroxyethyl)phenol]sulfide 2,2'-Bis[6-(2H-benzotriazole-2-yl)-4-(2-hydroxyethyl)phenol]sulfoxide 2,2'-Bis[6-(2H-benzotriazole-2-yl)-4-(2-hydroxyethyl)phenol]sulfone The bisbenzotriazolylphenol compound of the invention represented by the formula (1) can be produced by various methods. A preferred example is a method comprising the steps of:

reacting a benzotriazolylphenol compound of the formula

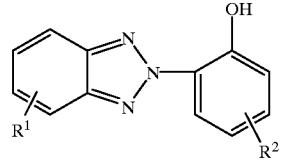

(2)

wherein $R^1$ and $R^2$ are as defined above, with an amine compound and a formaldehyde in a solvent to prepare a Mannich base compound represented by the formula

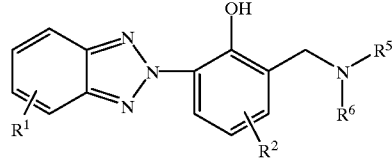

(3)

wherein $R^1$ and $R^2$ are as defined above, and $R^5$ and $R^6$ are the same or different and each represent a hydrogen atom or a $C_{1-8}$ alkyl group, or $R^5$ and $R^6$ are bonded to each other, and reacting the resultant Mannich base compound with the benzotriazolylphenol compound of the formula (2).

The benzotriazolylphenol compound of the formula (2) used as a starting material is a known compound which is produced, for example, by the method described in Japanese Examined Patent Publication No. 53733/1994. That is, an o-nitroaniline compound is reacted with sodium nitrite to prepare a diazonium salt represented by the formula

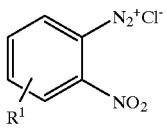

(4)

wherein $R^1$ is as defined above, which is then subjected to azo coupling under basic conditions with a phenol represented by the formula

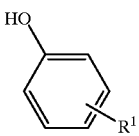

(5)

wherein $R^2$ is as defined above, giving a 2-[(2-nitrophenyl)azo]phenol compound represented by the formula

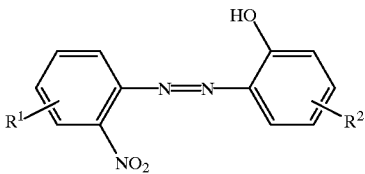

(6)

wherein $R^1$ and $R^2$ are as defined above. The obtained compound is reduced under basic conditions to prepare the benzotriazolylphenol compound represented by the formula (2).

Described below is the reaction of the benzotriazolylphenol compound of the formula (2) with an amine compound and a formaldehyde in a solvent to obtain the Mannich base compound of the formula (3).

The Mannich base compound of the formula (3) is produced by reacting the benzotriazolylphenol compound of the formula (2) with 1.0 to 3.0 equivalents each of an amine compound and a formaldehyde in a solvent for 1 to 30 hours.

The amine compound is not limited specifically and may be selected from a wide variety of conventionally known amine compounds. Preferably usable are primary amines such as monomethylamine, monoethylamine, monopropylamine, monobutylamine, monoamylamine, monohexylamine and the like; secondary amines such as dimethylamine, diethylamine, di-n-propylamine, diisopropylamine, di-n-butylamine, di-t-butylamine, diisobutylamine, diamylamine, dihexylamine, ethylmethylamine, methylisopropylamine, ethylisopropylamine and the like; cyclic amines such as morphorine, piperidine, pyrrolidine derivatives and the like.

The formaldehyde is not limited specifically and may be in the form of gas, liquid or solid. The formaldehyde may be selected from a wide variety of conventionally known formaldehydes. Specifically stated, preferably usable are formaldehyde and its aqueous solutions, straight-chain oligomers such as paraformaldehyde, cyclic oligomers such as trioxan and tetraoxymethylene, and the like.

The solvent may be any of known solvents which do not affect the reaction. Examples are lower alcohols such as methanol, ethanol, isopropanol, n-propanol, n-butanol, isobutanol, tert-butanol and the like; aliphatic hydrocarbons such as petroleum ether, hexane, heptane and the like; aromatic hydrocarbons such as benzene, toluene, xylene and the like; ethers such as diethyl ether, dibutyl ether, tetrahydrofuran, dioxane and the like; esters such as ethyl acetate, propyl acetate, butyl acetate and the like. These solvents can be used singly or two or more can be used as a mixture, depending on the purpose.

The amount of the solvent is not limited specifically and can be suitably selected from a wide range according to ease of stirring, reaction temperature, solubility of the substrate and other factors. However, it is usually preferred to use the solvent in an amount of 50 to 500 wt. % relative to the amount of the benzotriazolylphenol compound of the formula (2).

The reaction temperature is suitably selected from a range of 20 to 200° C., preferably 30 to 150° C., according to the kind of the solvent.

The bisbenzotriazolylphenol compound of the invention represented by the formula (1) is produced by reacting approximately equimolar amounts of the above-obtained Mannich base compound of the formula (3) and the benzotriazolylphenol compound of the formula (2) in the presence of an alkaline catalyst in a solvent for 1 to 100 hours.

Preferred alkaline catalysts include alkali metal alkoxides such as sodium methoxide, sodium ethoxide, sodium-n-propoxide and sodium isopropoxide, inorganic bases such as sodium hydroxide, potassium hydroxide, sodium carbonate and potassium carbonate, and the like. These catalysts can be used singly or as a mixture of two or more. The amount of the alkali catalyst is not limited specifically, but is preferably 0.01 to 10 wt. % relative to the amount of the Mannich base compound of the formula (3).

The solvent is not limited specifically and may be any of conventionally known solvents which do not affect the reaction. Examples are lower alcohols such as methanol, ethanol, isopropanol, n-propanol, n-butanol, isobutanol, tert-butanol and the like; aliphatic hydrocarbons such as petroleum ether, hexane, heptane and the like; aromatic hydrocarbons such as benzene, toluene, xylene and the like; ethers such as diethyl ether, dibutyl ether, tetrahydrofuran, dioxane and the like; esters such as ethyl acetate, propyl acetate, butyl acetate and the like. These solvents can be used singly or as a mixture of two or more, depending on the purpose. The amount of the solvent is not limited specifically, and can be selected according to ease of stirring, reaction temperature, solubility of the substrate and other factors. However, it is usually preferred to use the solvent in an amount of 50 to 500 wt. % relative to the amount of the Mannich base compound of the formula (3).

The reaction temperature is suitably selected from the range of 20 to 200° C., preferably 30 to 150° C., according to the kind of the solvent.

The bisbenzotriazolylphenol compound of the invention represented by the formula (1) is good in UV absorptivity, very low in vapor pressure and high in heat stability. Accordingly, the compound is very effective as a UV absorber for use in various resins including engineering plastics which are molded at high temperatures. The engineering plastics are not limited specifically and those conventionally known are usable. Examples are polypropylenes, cyclic polyolefins, polystyrenes, ABS resins, styrene maleimide resins, polyphenylene ethers, modified polyphenylene ethers, polycarbonates, polyacetals, polyamides, polyphenylene sulfides, polyesters, liquid crystal polymers, noncrystalline engineering plastics, polyimides, polyketones, polyurethanes and the like. The compound of the invention is particularly useful as a comonomer in condensation polymerization polymers such as polycarbonates, polyesters and polyurethanes.

The bisbenzotriazolylphenol compound of the invention, when mixed with the above resin, is used in a proportion of usually 0.01 to 30%, preferably 0.1 to 20% relative to the total weight of the compound and the resin. If the proportion is less than 0.01%, the resulting resin may have insufficient weather resistance, whereas a proportion exceeding 30% may impair the mechanical properties of the resin.

The composition comprising the above resin and the bisbenzotriazolylphenol compound of the invention may further contain one or more of other additives such as light stabilizer, antioxidant, plasticizer, fire retardant, antistatic agent, filler, pigment, coloring agent, etc., when necessary.

The bisbenzotriazolylphenol compound of the invention can be added to the resin (polymer) at any stage of the polymer production. Alternatively, the compound may be added to the polymer in a conventional manner before or during the molding process.

The bisbenzotriazolylphenol compound of the invention may be simply added to and dissolved in the polymer, but it is preferred to introduce the compound into the main chain or side chain of the polymer by copolymerizing the compound with a comonomer copolymerizable therewith and forming a carbonate bond, an ester bond, an ether bond, a urethane bond or like chemical bond. However, the compound can be introduced into the main chain of the polymer only when $R^2$ and $R^4$ in the formula (1) are both $C_{1-12}$ straight- or branched-chain hydroxyalkyl groups. A copolymer with a desired molecular weight is thus obtained which comprises the bisbenzotriazolylphenol compound of the invention as a comonomer, the copolymer having high light resistance and not losing its UV absorptivity by dissolution or transpiration.

The copolymer of the invention is not limited specifically insofar as it comprises the bisbenzotriazolylphenol compound of the invention as a copolymerization component. However, copolycarbonates, copolyesters, copolyurethanes and copolyurethaneureas are important in the invention.

The copolycarbonate, copolyester, copolyurethane and copolyurethaneurea of the invention are similar to conventional polycarbonates, polyesters, polyurethanes and polyurethaneureas, respectively, with the exception that those of the invention contain the bisbenzotriazolylphenol compound of the formula (1) introduced into the main chain as a copolymer component. The polymers of the invention can be produced in the similar manner as in the production of conventional polycarbonates, polyesters, polyurethanes or polyurethaneureas.

The copolycarbonate of the invention can be produced, for example, by the interfacial polymerization method or pyridine method described below.

The interfacial polymerization method is carried out as follows. The bisbenzotriazolylphenol compound of the formula (1) and a divalent phenolic compound are reacted with phosgene in a two-phase system of an organic solvent inert to the reaction and an alkali aqueous solution, optionally in the presence of a molecular weight modifier and/or end terminator. Subsequently, a polymerization catalyst such as a tertiary amine or quaternary amine is added to carry out copolymerization, whereby the objective copolycarbonate can be produced. In the above method, the bisbenzotriazolylphenol compound of the formula (1) may be first reacted with phosgene to prepare a dichloroformate, which is then polymerized by addition of the divalent phenolic compound. Alternatively, the dichloroformate of the divalent phenolic compound may be first prepared and then copolymerized by addition of the bisbenzotriazolylphenol compound of the formula (1).

The pyridine method comprises the steps of dissolving the bisbenzotriazolylphenol compound of the formula (1) and a divalent phenolic compound, optionally together with a molecular weight modifier and/or end terminator, in pyridine or a mixed solvent of pyridine and an organic solvent inert to the reaction, and blowing phosgene into the solution to directly obtain a copolycarbonate.

The divalent phenolic compound for use in the copolycarbonate production can be selected from a wide variety of conventionally known divalent phenolic compounds. Examples are bis(4-hydroxyphenyl)methane, bis(4-hydroxyphenyl)ether, bis(4-hydroxyphenyl)sulfone, bis(4-hydroxyphenyl)sulfoxide, bis(4-hydroxyphenyl) sulfide, bis (4-hydroxyphenyl)ketone, 1,1-bis(4-hydroxyphenyl)ethane, 2,2-bis(4-hydroxyphenyl)propane, 2,2-bis(4-hydroxyphenyl) butane, 1,1-bis(4-hydroxyphenyl) cyclohexane, 2,2-bis(4-hydroxy-3,5-dibromophenyl) propane, 2,2-bis(4-hydroxy-3,5-dichlorophenyl)propane, 2,2-bis(4-hydroxy-3-bromophenyl) propane, 2,2-bis(4-hydroxy-3-chlorophenyl)propane, 2,2-bis(4-hydroxy-3,5-dimethylphenyl)propane, 1,1-bis(4-hydroxyphenyl)-1-phenylethane and the like. These compounds can be used singly or as a mixture of two or more.

The polymerization catalyst may be selected from a wide variety of conventionally known polymerization catalysts. Examples are tertiary amines such as trimethylamine, triethylamine, tributylamine, tripropylamine, trihexylamine, tridecylamine, N,N-dimethylcyclohexylamine, pyridine, quinoline and dimethylaniline, quaternary ammonium salts such as trimethylbenzylammonium chloride, tetramethylammonium chloride and triethylbenzylammonium chloride, and the like.

The reaction solvent is preferably inert to the reaction, and include hydrocarbon halides such as dichloromethane, chloroform, 1,2-dichloroethane, 1,1,2,2-tetrachloroethane, 1,1,1-trichloroethane, carbon tetrachloride, monochlorobenzene, dichlorobenzene and the like; aromatic hydrocarbons such as benzene, toluene, xylene, ethylbenzene and the like; ethers such as diethyl ether, dibutyl ether and the like. These organic solvents can be used singly or as a mixture of two or more. When desired, ketones, esters, nitriles or like hydrophilic solvents not mentioned above can be used as mixed with other solvents, so that the mixed solvent is not completely compatible with water.

The molecular weight modifier and end terminator are usually compounds having a monovalent phenolic hydroxyl group. Examples of such compounds include phenol, p-tert-butylphenol, tribromophenol, long-chain alkylphenol and the like. These compounds are used in an amount of 0.5 to 50 mol %, preferably 1 to 30 mol %, relative to the total amount of the polycondensation monomers (bisbenzotriazolylphenol compound, divalent phenolic compound and phosgene), and may be used singly or as a mixture of two or more.

The bisbenzotriazolylphenol compound of the formula (1) is used in the copolycarbonate production in an amount of 0.01 to 99.9 wt. %, preferably 0.1 to 70 wt. % relative to the amount of the comonomer (divalent phenolic compound). The comonomer may be of one kind, or two or more kinds of comonomers may be used as a mixture.

The copolycarbonate of the invention is produced mainly from the above components. In addition, a branching agent may be used in an amount of 0.01 to 3 mol %, preferably 0.1 to 1.0 mol %, relative to the total amount of the polycondensation monomers to prepare a branched copolycarbonate.

Usable branching agents include polyhydroxy compounds such as fluoroglycine, 2,6-dimethyl-2,4,6-tri(4-hydroxyphenyl)-2-hepten, 2,6-dimethyl-2,4,6-tri(4-hydroxyphenyl)-3-hepten, 1,3,5-tri(2-hydroxyphenyl)ethane, 2,6-bis(2-hydroxyphenyl)benzol, 1,1,1-tri(4-hydroxyphenyl)ethane, 2,6-bis(2-hydroxy-5-methylbenzyl)-4-methylphenol and the like; isatins such as 3,3-bis(4-hydroxyaryl)oxyindol, 5-chloroisatin, 5,7-dichloroisatin, 5-bromoisatin and the like.

The copolyester of the invention can be produced, for example, by the following methods.

A mixture of a diol and the bisbenzotriazolyl-phenol compound of the formula (1) is subjected to ester exchange with a lower alkylester of a dicarboxylic acid, and the reaction mixture was further subjected to polycondensation to obtain the objective copolyester. Alternatively, the bisbenzotriazolylphenol compound of the formula (1) and a diol are subjected to dehydrocondensation with a dicarboxylic acid to carry out polycondensation, whereby the copolyester is produced.

The bisbenzotriazolylphenol compound of the formula (1) is used in the copolyester production in an amount of 0.01 to 50 mol %, preferably 0.1 to 30 mol %, relative to the total amount of the comonomers (diol and dicarboxylic acid). If the amount is less than 0.01 mol %, it is difficult to impart sufficient weather resistance to the copolyester, whereas an amount exceeding 70 mol % may diminish the properties of the copolyester. Each of the comonomers may be of a single kind, or two or more kinds of each comonomer may be used as a mixture.

The diol may be selected from a wide variety of conventionally known diols. Examples are ethylene glycol, propylene glycol, tetramethylene glycol, hexamethylene glycol, nonamethylene glycol, cyclohexane dimethanol, diethylene glycol and the like. They may be used singly or as a mixture of two or more. The copolyester may further contain as a comonomer a polyfunctional compound with a valency of three or more within a range that permits melt-molding of the resulting copolyester. Examples of said polyfunctional compound are glycerine, trimethylolpropane, pentaerythritol, trimellitic acid, trimesic acid, pyromellitic acid and the like.

The dicarboxylic acid may be selected from a wide variety of conventionally known dicarboxylic acids. Examples are aromatic dicarboxylic acids such as terephthalic acid, isophthalic acid, 2,6-naphthalenedicarboxylic acid and the like; aliphatic dicarboxlic acids such as adipic acid, azelaic acid, sebacic acid and the like. The amount of the dicarboxylic acid is not limited specifically, but preferably 50 mol % or more relative to the total amount of the monomers. The dicarboxylic acids may be used singly or as a mixture of two or more.

The copolyurethane of the invention can be produced, for example, by the following methods.

A glycol and the bisbenzotriazolylphenol compound of the formula (1) are subjected to polyaddition with a diisocyanate to obtain the objective copolyurethane, or bischloroformic acid ester of the bisbenzotriazolylphenol compound of the formula (1) and bischloroformic acid ester of a glycol are reacted with diamine to obtain the copolyurethane, or a glycol and the bisbenzotriazolylphenol compound of the formula (1) are subjected to ester exchange with a biscarbamic acid ester to obtain the copolyurethane. In particular, the method using a diisocyanate is industrially advantageous.

The bisbenzotriazolylphenol compound of the formula (1) is used in the copolyurethane production in an amount of 0.1 to 50 mol %, preferably 1 to 30 mol %, relative to the amount of the copolymer (copolyurethane consisting of the bisbenzotriazolylphenol compound, diisocyanate and glycol). If the amount is less than 0.1 mol %, it is difficult to impart sufficient weather resistance to the copolyurethane, whereas an amount exceeding 50 mol % may diminish the properties of the copolyurethane. Each of the comonomers may be of a single kind, or two or more kinds of each comonomer may be used as a mixture.

The diisocyanate may be selected from a wide variety of conventionally known diisocyanates. Examples are aliphatic diisocyanates such as propylene diisocyanate, tetramethylene diisocyanate, hexamethylene diisocyanate, nanomethylene diisocyanate, cyclohexane diisocyanate and the like; aromatic diisocyanates such as 1,4-phenylene diisocyanate, 1,3-phenylene diisocyanate, 2,6-tolylene diisocyanate, 2,4-tolylene diisocyanate and the like. The amount of the diisocyanate is not limited specifically, but is preferably 50 mol % or more relative to the total amount of the monomers. The diisocyanates can be used singly or as a mixture of two or more.

The glycol may be selected from a wide variety of conventionally known glycols. Examples are ethylene glycol, propylene glycol, tetramethylene glycol, heptamethylene glycol, hexamethylene glycol, octamethylene diol, nonamethylene glycol, cyclohexane dimethanol, diethylene glycol and the like. They can be used singly or as a mixture of two or more.

The biscarbamic acid ester for use in the ester exchange with the glycol includes aliphatic biscarbamic acid esters such as ethyl propylenebiscarbamate, ethyl tetramethylenebiscarbamate, ethyl hexamethylenebiscarbamate, ethyl nanomethylenedibiscarbamate, ethyl cyclohexanedibiscarbamate, n-propyl propylene biscarbamate, n-propyl tetramethylenebiscarbamate, n-propyl hexamethylenebiscarbamate, n-butyl propylenebiscarbamate, n-butyl tetramethylenebiscarbamate, n-butyl hexamethylenebiscarbamate and the like; aromatic biscarbamic acid esters such as ethyl 1,4-phenylenebiscarbamate, ethyl 1,3-phenylenebiscarbamate, ethyl 2,6-tolylenebiscarbamate, ethyl 2,4-tolylenebiscarbamate, n-propyl 1,4-phenylenebiscarbamate, n-propyl 1,3-phenylenebiscarbamate, n-propyl 2,6-tolylenebiscarbamate, n-propyl 2,4-tolylenebiscarbamate, n-butyl 1,4-phenylenebiscarbamate, n-butyl 1,3-phenylenebiscarbamate, n-butyl 2,6-tolylenebiscarbamate, n-butyl 2,4-tolylenebiscarbamate and the like. The amount of the biscarbamic acid ester is not limited specifically, but is preferably 50 mol % or more relative to the total amount of the monomers. The biscarbamic acids may be used singly or as a mixture of two or more.

The UV absorptive copolymer whose main chain or side chain has the bisbenzotriazolylphenol compound of the formula (1) introduced by a chemical bond may be used singly or as a nonvolatile UV absorber which is mixed with a resin composition during the production of the resin composition. When the UV absorptive copolymer whose main chain or side chain has a unit of the bisbenzotriazolylphenol compound of the formula (1) introduced by a chemical bond is used as diluted with a polymer compatible with said compound, the unit of the bisbenzotriazolylphenol compound of the formula (1) is used in such an amount that the diluted polymer contains 0.01 to 30 wt. % of said unit.

The copolymer of the invention and the composition comprising said copolymer may contain one or more of other additives when necessary, which include light stabilizer, antioxidant, fire retardant, antistic agent, plasticizer, filler, pigment, coloring agent or the like.

The copolymer of the invention and the composition comprising said copolymer have excellent UV absorptivity, and thus exhibit particularly good effects when used for purposes requiring high weather resistance.

Like conventional polymers, the copolymer of the invention and the composition comprising said copolymer can be molded by known molding methods such as injection molding, extrusion molding, blow molding, biaxal centrifugal blow molding, press molding and melt spinning. Further, said copolymer or composition may be dissolved or dispersed in a suitable solvent or aqueous system for use as a coating composition.

Molded articles obtained from the copolymer of the invention or the composition comprising said copolymer have high weather resistance and thus exhibit particularly high performance when used in situations directly exposed to UV rays or sunlight, as for building materials, carports, sound barriers, agricultural or industrial films and sheets, weather resistant coating compositions and weather resistant fibers.

Packaging materials, coatings for containers and like molded articles obtained from the copolymer of the invention or the composition comprising said copolymer have excellent UV absorptivity and thus can be preferably used for purposes in which interception of UV rays are required for protecting the contents.

BEST MODE FOR CARRYING OUT THE INVENTION

The following Examples illustrate the present invention in further detail. In the Examples, "part(s)" means "part(s) by weight".

EXAMPLE 1

15.4 g (110 mmols) of o-nitroaniline was added to 42 ml of concentrated hydrochloric acid, followed by stirring at 70° C. for about 30 minutes. The mixture was cooled to 0° C. in an ice bath. Subsequently, a previously prepared aqueous solution of 7.9 g (110 mmols) of sodium nitrite in 28 ml of water was added dropwise over a period of about 1 hour. During the addition, the mixture was maintained at 5° C. or less. The obtained mixture was further stirred for 1 hour at 5° C. or less, giving diazonium salt of o-nitroaniline.

EXAMPLE 2

19.2 g (110 mmols) of 4-chloro-2-nitroaniline was added to 42 ml of concentrated hydrochloric acid, followed by stirring at 70° C. for about 30 minutes. The mixture was then cooled to 0° C. in an ice bath. Subsequently, a previously prepared aqueous solution of 7.9 g (110 mmols) of sodium nitrite in 28 ml of water was added dropwise over a period of about 1 hour. During the addition, the mixture was maintained at 5° C. or less. The obtained mixture was further stirred for 1 hour at 5° C. or less, giving diazonium salt of 4-chloro-2-nitroaniline.

EXAMPLE 3

In 150 ml of water were dissolved 13.8 g (100 mmols) of p-hydroxyphenethyl alcohol, 4.0 g (100 mmols) of sodium hydroxide and 30 g (0.36 mmols) of sodium carbonate. A hydrochloric acid solution of diazonium salt of o-nitroaniline synthesized in Example 1 was added dropwise over a period of about 1 hour. During the addition, the mixture was maintained at about 15° C. After completion of the addition, the resulting mixture was stirred at room temperature for 12 hours. Precipitated crystals were collected by filtration and dried under reduced pressure, giving 27.6 g of 4-(2-hydroxyethyl)-2-[(2-nitrophenyl)azo]phenol as red crystals (yield 94%, purity 97%).

$^1$H-NMR(CDCl$_3$): δ=2.92 (t, 2H, CH$_2$), 3.92 (t, 2H, CH$_2$OH), 7.03(d, 1H, Ar—H), 7.30 (dd, 1H, Ar—H), 7.60 (t, 1H, Ar—H), 7.74 (t, 1H, Ar—H), 7.84 (s, 1H, Ar—H), 7.96 (d, 1H, Ar—H), 8.10 (d, 1H, Ar—H), 12.22 (s, 1H, Ar—OH)

EXAMPLE 4

In 150 ml of water were dissolved 13.8 g (100 mmols) of p-hydroxyphenethyl alcohol, 4.0 g (100 mmols) of sodium hydroxide and 30 g (0.36 mmols) of sodium carbonate. A hydrochloric acid solution of diazonium salt of 4-chloro-2-nitroaniline obtained in Example 2 was added dropwise over a period of about 1 hour. The subsequent treatment was carried out in the same manner as in Example 3, giving 23.7 g of 4-(2-hydroxyethyl)-2-[(4-chloro-2-nitrophenyl)azo]phenol as red crystals (yield 72%, purity 98%).

$^1$H-NMR(CDCl$_3$): δ=2.92 (t, 2H, CH$_2$), 3.92 (t, 2H, CH$_2$OH), 7.03 (d, 1H, Ar—H), 7.30 (dd, 1H, Ar—H), 7.70 (d, 1H, Ar—H), 7.82 (s, 1H, Ar—H), 7.96 (d, 1H, Ar—H), 8.08 (s, 1H, Ar—H), 12.14 (s, 1H, Ar—OH)

EXAMPLE 5

In 150 ml of water were dissolved 15.2 g (100 mmols) of 4-(3-hydroxypropyl)phenol, 4.0 g (100 mmols) of sodium hydroxide and 30 g (0.36 mmols) of sodium carbonate. A hydrochloric acid solution of diazonium salt of o-nitroaniline obtained in Example 1 was added dropwise over a period of about 1 hour. The subsequent treatment was carried out in the same manner as in Example 3, giving 29.1 g of 4-(3-hydroxypropyl)-2-[(2-nitrophenyl)azo]phenol as red crystals (yield 91%, purity 94%).

$^1$H-NMR(CDCl$_3$): δ=1.89 (q, 2H, Ar—CH$_2$—), 2.65 (t, 2H, CH$_2$), 3.70 (t, 2H, CH$_2$OH), 7.03 (d, 1H, Ar—H), 7.30 (dd, 1H, Ar—H), 7.60 (t, 1H, Ar—H), 7.74 (t, 1H, Ar—H), 7.84 (s, 1H, Ar—H), 7.96 (d, 1H, Ar—H), 8.10 (d, 1H, Ar—H), 12.22(s, 1H, Ar—OH)

EXAMPLE 6

5.39 g (18 mmols) of crude 4-(2-hydroxyethyl)-2-[(2-nitrophenyl)azo]phenol synthesized in Example 3 was dissolved in 18 ml of aqueous solution of 2N sodium hydroxide. Subsequently, 9 ml of previously prepared aqueous solution of 25% sodium hydroxide and 5.4 g (83 mmols) of zinc powder were simultaneously added over a period of about 3 hours. The reaction mixture was heated to 70° C. and stirred for about 2 hours. The reaction mixture was then cooled to room temperature and filtered to collect inorganic substance. The obtained mother liquor was acidified with concentrated hydrochloric acid. Precipitated crystals were collected by filtration and recrystalized in toluene, giving 3.70 g of 2-(2H-benzotriazole-2-yl)-4-(2-hydroxyethyl)phenol as yellow crystals (yield 70%, purity 87%).

$^1$H-NMR(CDCl$_3$): δ=2.92 (t, 2H, CH$_2$), 3.93 (t, 2H, CH$_2$OH), 7.15 (d, 1H, Ar—H), 7.23 (dd, 1H, Ar—H),7.49 (m, 2H, Ar—H), 7.94 (m, 2H, Ar—H), 8.28 (s, 1H, Ar—H), 11.22 (s, 1H, Ar—OH)

EXAMPLE 7

5.91 g (18 mmols) of crude 4-(2-hydroxyethyl)-2-[(4-chloro-2-nitrophenyl)azo]phenol synthesized in Example 4 was dissolved in 18 ml of aqueous solution of 2N sodium hydroxide. Subsequently, 9 ml of previously prepared aqueous solution of 25% sodium hydroxide and 5.4 g (83 mmols) of zinc powder were simultaneously added over a period of about 3 hours. The subsequent treatment was carried out in the same manner as in Example 6, giving 4.02 g of 2-(5-chloro-2H-benzotriazole-2-yl)-4-(2-hydroxyethyl)phenol as pale yellow crystals (yield 68%, purity 88%).

$^1$H-NMR(CDCl$_3$): δ=2.85 (t, 2H, CH$_2$), 3.85 (t, 2H, CH$_2$OH), 7.05(d, 1H, Ar—H), 7.10 (dd, 1H, Ar—H), 7.37 (d, 1H, Ar—H), 7.82 (d, 1H, Ar—H), 7.84 (s, 1H, Ar—H), 8.16 (s, 1H, Ar—H), 10.82 (s, 1H, Ar—OH)

EXAMPLE 8

5.60 g (18 mmols) of crude 4-(3-hydroxypropyl)-2-[(2-nitrophenyl)azo]phenol synthesized in Example 5 was dissolved in 18 ml of aqueous solution of 2N sodium hydroxide. Subsequently, 9 ml of previously prepared aqueous solution of 25% sodium hydroxide and 5.4 g (83 mmols) of zinc powder were simultaneously added over a period of about 3 hours. The subsequent treatment was carried out in the same manner as in Example 6, giving 3.92 g of 2-(2H-benzotriazole-2-yl)-4-(3-hydroxypropyl)phenol as pale yellow crystals (yield 72%, purity 89%).

$^1$H-NMR(CDCl$_3$): δ=1.89 (q, 2H, Ar—CH$_2$—), 2.67 (t, 2H, CH$_2$), 3.78 (t, 2H, CH$_2$OH), 7.15 (d, 1H, Ar—H), 7.23 (dd, 1H, Ar—H), 7.49 (m, 2H, Ar—H), 7.94 (m, 2H, Ar—H), 8.28 (s, 1H, Ar—H), 11.22 (s, 1H, Ar—OH)

EXAMPLE 9

In 25 ml of n-butanol were dissolved 25.5 g (0.1 mols) of the purified product of 2-(2H-benzotriazole-2-yl)-4-(2-hydroxyethyl)phenol synthesized in Example 6, 5.2 g of 80% paraformaldehyde and 11.0 g (0.15 mols) of diethylamine. The solution was refluxed with heating at 105° C. for 24 hours. After completion of the reaction, the solvent and remaining raw materials were collected under reduced pressure, giving 34.7 g of objective 2-(2H-benzotriazole-2-yl)-4-(2-hydroxyethyl)-6-(N,N-diethylaminomethyl)phenol as a brown oil (yield 98.9%, purity 96.9%).

$^1$H-NMR(CDCl$_3$): δ=1.10 (t, 6H, CH$_3$), 2.66 (q, 4H, N—CH$_2$), 2.85 (t, 2H, CH$_2$), 3.87 (t, 2H, CH$_2$OH), 7.04 (s, 1H, Ar—H), 7.42 (dd, 2H, Ar—H), 7.62 (s, 1H, Ar—H), 7.97 (dd, 2H, Ar—H)

EXAMPLE 10

In 25 ml of n-butanol were dissolved 29.0 g (0.1 mols) of the purified product of 2-(5-chloro-2H-benzotriazole-2-yl)-4-(2-hydroxyethyl)phenol synthesized in Example 7, 5.2 g of 80% paraformaldehyde and 11.0 g (0.15 mols) of diethylamine. The solution was refluxed with heating at 105° C. for 24 hours. After completion of the reaction, the solvent and remaining raw materials were collected under reduced pressure, giving 37.0 g of objective 2-(5-chloro-2H-benzotriazole-2-yl)-4-(2-hydroxyethyl)-6-(N,N-diethylaminomethyl)phenol as a brown oil (yield 93.9%, purity 95.0%).

$^1$H-NMR(CDCl$_3$): δ=1.10 (t, 6H, CH$_3$), 2.66 (q, 4H, N—CH$_2$), 2.85 (t, 2H, CH$_2$), 3.87 (t, 2H, CH$_2$OH), 7.04 (s, 1H, Ar—H), 7.37 (d, 1H, Ar—H), 7.62 (s, 1H, Ar—H), 7.82 (d, 1H, Ar—H), 7.84 (s, 1H, Ar—H)

EXAMPLE 11

In 25 ml of n-butanol were dissolved 26.9 g (0.1 mols) of the purified product of 2-(2H-benzotriazole-2-yl)-4-(3-hydroxypropyl)phenol synthesized in Example 8, 5.2 g of 80% paraformaldehyde and 11.0 g (0.15 mols) of diethylamine. The solution was refluxed with heating at 105° C. for 24 hours. After completion of the reaction, the solvent and remaining raw materials were collected under reduced pressure, giving 35.9 g of objective 2-(2H-benzotriazole-2-yl)-4-(3-hydroxypropyl)-6-(N,N-diethylaminomethyl) phenol as a brown oil (yield 97.0%, purity 95.6%).

$^1$H-NMR(CDCl$_3$): δ=1.10 (t, 6H, CH$_3$), 1.89 (q, 2H, Ar—CH$_2$—), 2.66 (q, 4H, N—CH$_2$), 2.70 (t, 2H, CH$_2$), 3.81 (t, 2H, CH$_2$OH), 7.04 (s, 1H, Ar—H), 7.42 (dd, 2H, Ar—H), 7.62 (s, 1H, ArH), 7.97 (dd, 2H, Ar—H)

EXAMPLE 12

In 100 ml of xylene were dissolved 34.7 g of crude 2-(2H-benzotriazole-2-yl)-4-(2-hydroxyethyl)-6-(N,N-diethylaminomethyl)phenol synthesized in Example 9 and 25.5 g (0.1 mols) of the purified product of 2-(2H-benzotriazole-2-yl)-4-(2-hydroxyethyl)phenol synthesized in Example 6. 5 ml of methanol solution of 28% sodium methylate was added, and the mixture was refluxed in a nitrogen stream for 10 hours. After completion of the reaction, the reaction mixture was cooled to room temperature. Precipitated yellow crystals were collected by filtration and recrystallized in chloroform, giving 28.5 g of 2,2'-methylenebis[6-(2H-benzotriazole-2-yl)-4-(2-hydroxyethyl)phenol] as white crystals (yield 54%, purity 98.9%).

$^1$H-NMR(CDCl$_3$): δ=2.89 (t, 4H, CH$_2$), 3.89 (t, 4H, CH$_2$OH), 4.28 (s, 2H, CH$_2$), 7.26 (s, 2H, Ar—H), 7.47 (dd, 4H, Ar—H), 7.92 (dd, 4H, Ar—H), 8.18 (s, 2H, Ar—H), 11.56 (s, 2H, Ar—OH)

EXAMPLE 13

In 100 ml of xylene were dissolved 37.0 g (93.9 mmols) of crude 2-(5-chloro-2H-benzotriazole-2-yl)-4-(2-hydroxyethyl)-6-(N,N-diethylaminomethyl)phenol synthesized in Example 10 and 27.2 g (93.9 mmols) of the purified product of 2-(5-chloro-2H-benzotriazole-2-yl)-4-(2-hydroxyethyl)phenol synthesized in Example 7. 5 ml of methanol solution of 28% sodium methylate was added, and the mixture was refluxed in a nitrogen stream for 10 hours. The subsequent treatment was carried out in the same manner as in Example 12, giving 30.8 g of 2,2'-methylenebis [6-(5-chloro-2H-benzotriazole-2-yl)-4-(2-hydroxyethyl) phenol] as pale yellow crystals (yield 55.0%, purity 99.0%).

$^1$H-NMR(CDCl$_3$): δ=2.89 (t, 4H, CH$_2$), 3.89 (t, 4H, CH$_2$OH), 4.28 (s, 2H, CH$_2$), 7.26 (s, 2H, Ar—H), 7.37 (d, 2H, Ar—H), 7.82 (d, 2H, Ar—H), 7.84 (s, 2H, Ar—H), 8.18 (s, 2H, Ar—H), 11.59 (s, 2H, Ar—OH)

EXAMPLE 14

In 100 ml of xylene were dissolved 35.9 g (97.0 mmols) of crude 2-(2H-benzotriazole-2-yl)-4-(3-hydroxypropyl)-6-(N,N-diethylaminomethyl)phenol synthesized in Example 11 and 26.1 g (97.0 mmols) of the purified product of 2-(2H-benzotriazole-2-yl)-4-(3-hydroxypropyl)phenol synthesized in Example 6. 5 ml of a methanol solution of 28% sodium methylate was added, and the mixture was refluxed in a nitrogen stream for 10 hours. The subsequent treatment was carried out in the same manner as in Example 12, giving 33.0 g of 2,2'-methylenebis[6-(2H-benzotriazole-2-yl)-4-(3-hydroxypropyl)phenol] as white crystals (yield 61.2%, purity 99.0%).

$^1$H-NMR(CDCl$_3$): δ=1.89 (q, 2H, Ar—CH$_2$—), 2.82 (t, 4H, CH$_2$), 3.81 (t, 4H, CH$_2$OH), 4.28 (s, 2H, CH$_2$), 7.26 (s,

2H, Ar—H), 7.47 (dd, 4H, Ar—H), 7.92 (dd, 4H, Ar—H), 8.18 (s, 2H, Ar—H), 11.59 (s, 2H, Ar—OH)

EXAMPLE 15

In 150 ml of water were dissolved 16.6 g (100 mmols) of 4-(4-hydroxybutyl)phenol, 4.0 g (100 mmols) of sodium hydroxide and 30 g (0.36 mmols) of sodium carbonate. A hydrochloric acid solution of diazonium salt of o-nitroaniline synthesized in Example 1 was added dropwise over a period of about 1 hour. The subsequent treatment was carried out in the same manner as in Example 3, giving 30.2 g of 4-(4-hydroxybutyl)-2-[(2-nitrophenyl)azo]phenol as red crystals (yield 90%, purity 94%).

$^1$H-NMR(CDCl$_3$): δ=1.55 (m, 4H, CH$_2$), 2.52 (t, 2H, Ar—CH$_2$), 3.02 (t, 2H, CH$_2$OH), 7.03 (d, 1H, Ar—H), 7.31 (dd, 1H, Ar—H), 7.63 (t, 1H, Ar—H), 7.75 (t, 1H, Ar—H), 7.82 (s, 1H, Ar—H), 7.96 (d, 1H, Ar—H), 8.10 (d, 1H, Ar—H), 12.22 (s, 1H, Ar—OH)

EXAMPLE 16

6.03 g (18 mmols) of crude 4-(4-hydroxybutyl)-2-[(2-nitrophenyl)azo]phenol synthesized in Example 15 was dissolved in 18 ml of aqueous solution of 2N sodium hydroxide. 9 ml of previously prepared aqueous solution of 25% sodium hydroxide and 5.4 g (83 mmols) of zinc powder were simultaneously added over a period of about 3 hours. The subsequent treatment was carried out in the same manner as in Example 6, giving 4.41 g of 2-(2H-benzotriazole-2-yl)-4-(4-hydroxybutyl)phenol as pale yellow crystals (yield 78%, purity 90%).

$^1$H-NMR(CDCl$_3$): δ=1.55 (m, 4H, CH$_2$), 2.52 (t, 2H, Ar—CH$_2$), 3.02 (t, 2H, CH$_2$OH), 7.15 (d, 1H, Ar—H), 7.23 (dd, 1H, Ar—H), 7.49 (m, 2H, Ar—H), 7.94 (m, 2H, Ar—H), 8.28 (s, 1H, Ar—H), 11.22 (s, 1H, Ar—OH)

EXAMPLE 17

In 25 ml of n-butanol were dissolved 28.3 g (0.1 mols) of the purified product of 2-(2H-benzotriazole-2-yl)-4-(4-hydroxybutyl)phenol synthesized in Example 16, 5.2 g of 80% paraformaldehyde and 11.0 g (0.15 mols) of diethylamine. The solution was refluxed with heating at 105° C. for 24 hours. After completion of the reaction, the solvent and remaining raw materials were collected under reduced pressure, giving 37.4 g of objective 2-(2H-benzotriazole-2-yl)-4-(4-hydroxybutyl)-6-(N,N-diethylaminomethyl)phenol as a brown oil (yield 97.0%, purity 95.6%).

$^1$H-NMR(CDCl$_3$): δ=1.10 (t, 6H, CH$_3$), 1.55 (m, 4H, CH$_2$), 2.66 (q, 4H, N—CH$_2$), 2.52 (t, 2H, Ar—CH$_2$), 3.02 (t, 2H, CH$_2$OH), 7.04 (s, 1H, Ar—H), 7.42 (dd, 2H, Ar—H), 7.62 (s, 1H, Ar—H), 7.97 (dd, 2H, Ar—H)

EXAMPLE 18

In 100 ml of xylene were dissolved 37.3 g (97.0 mmols) of crude 2-(2H-benzotriazole-2-yl)-4-(4-hydroxybutyl)-6-(N,N-diethylaminomethyl)phenol synthesized in Example 17 and 26.1 g (97.0 mmols) of the purified product of 2-(2H-benzotriazole-2-yl)-4-(4-hydroxybutyl) phenol synthesized in Example 16. 5 ml of methanol solution of 28% sodium methylate was added, and the mixture was refluxed in a nitrogen stream for 10 hours. The subsequent treatment was carried out in the same manner as in Example 12, giving 37.0 g of 2,2'-methylenebis[6-(2H-benzotriazole-2-yl)-4-(4-hydroxybutyl)phenol as white crystals (yield 65.3%, purity 99.0%).

$^1$H-NMR(CDCl$_3$): δ=1.55 (m, 8H, CH$_2$), 2.52 (t, 2H, Ar—CH$_2$), 3.02 (t, 4H, CH$_2$OH), 4.28 (s, 2H, CH$_2$), 7.26 (s, 2H, Ar—H), 7.47 (dd, 4H, Ar—H), 7.92 (dd, 4H, Ar—H), 8.18 (s, 2H, Ar—H), 11.59 (s, 2H, Ar—OH)

EXAMPLE 19

In 60 ml of pyridine were dissolved 0.154 g (0.295 mmols) of 2,2'-methylenebis[6-(2H-benzotriazole-2-yl)-4-(2-hydroxyethyl)phenol] synthesized in Example 12 and 1.72 g (7.16 mmols) of bisphenol A. 2.08 g (6.87 mmols) of triphosgene was gradually added with stirring in a nitrogen stream. After further 1-hour stirring at room temperature, 250 ml of methanol was added to precipitate a polymer. The polymer was collected by filtration and dried under reduced pressure, giving 2.23 g of polycarbonate (copolycarbonate) as a white polymer, which contained 5.1 wt. % of 2,2'-methylenebis[6-(2H-benzotriazole-2-yl)-4-(2-hydroxyethyl)phenol (yield 85.3%).

The UV spectra of 2,2'-methylenebis[6-(2H-benzotriazole-2-yl)-4-(2-hydroxyethyl)phenol] and the polymer were determined to calculate the benzotriazole content from the absortivity cofficient ratio of the two substances.

Test Example 1

105 parts of the copolycarbonate synthesized in Example 19 was dissolved in 630 parts of 1,1,2,2-tetrachloroethane. The solution was applied to a circular quartz plate with a diameter of 300 mm using a spinner.

The obtained coating was air-dried for 1 hour and then dried under reduced pressure at 60° C. for 12 hours to form on the plate a uniform thin film with a thickness of about 1 μm. The film was subjected to a 1200-hour accelerated weathering test using a Dew cycle sunshine Super Long-Life Weather Meter WEL-SUN-DC (product of Test Instruments Co., Ltd., 18-minute rainfall every 120 minutes). Thereafter, the polycarbonate thin film was checked for the degree of yellowness (ΔYI)(Test Example 1). For comparison, 100 parts of commercially available polycarbonate resin not containing a UV absorber (tradename: E-2000, product of Mitsubishi Gas Chemical Co., Inc.) was dissolved in 630 parts of 1,1,2,2-tetrachloroethane. To the solution was added 5 parts of the following UV absorber A (Comparison A) or 5 parts of the following UV absorber B (Comparison B). The obtained compositions were formed into films and subjected to the accelerated weathering test in the same manner as in Test Example 1 to determine the degree of yellowness (ΔYI) of the resin films. Table 1 shows the amounts of the components (parts=wt. parts) and the degree of yellowness (ΔYI) of the resin films. The resin films containing UV absorber A or B clearly yellowed, whereas the copolycarbonate of Example 19 was substantially free from yellowing and found to have very high weather resistance.

TABLE 1

|  | Test Ex. 1 | Comp. A | Comp. B |
|---|---|---|---|
| Commercial polycarbonate | — | 100 parts | 100 parts |
| Copolycarbonate of Ex. 19 | 105 parts | — | — |
| 1,1,2,2-Tetrachloroethane | 630 parts | 630 parts | 630 parts |
| UV absorber A | — | 5.0 parts | — |
| UV absorber B | — | — | 5.0 parts |

TABLE 1-continued

| | Test Ex. 1 | Comp. A | Comp. B |
|---|---|---|---|
| Degree of yellowness (ΔYI) after 1200-hr test | 0.1 | 2.1 | 2.3 |

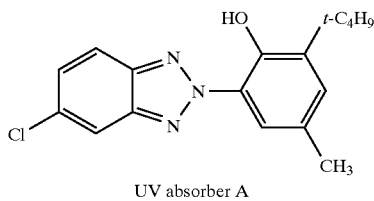

UV absorber A

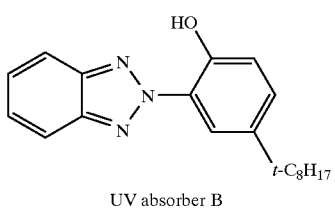

UV absorber B

EXAMPLE 20

Mixed together were 100 g (0.52 mols) of dimethyl terephthalate, 72 g (1.16 mols) of ethylene glycol and 30 mg of manganese acetate tetrahydrate. The mixture was heated to 140° C., and then further heated to 240° C. with stirring over a period of about 3 hours to distill off about 15 g of methanol. To the mixture was added 10 mg of phosphorous acid, 50 mg of germanium dioxide and 8.53 g (1.6 mmols) of 2,2'-methylenebis[6-(2H-benzotriazole-2-yl)-4-(2-hydroxyethyl)phenol] synthesized in Example 12. The resulting mixture was subjected to polycondensation at 280° C. and 0.5 mmHg for about 2 hours, giving 148.3 g of objective copolyester as a pale brown solid. The intrinsic viscosity (η) of the polyester was 0.82, and the UV absorber content in the copolyester was 5.02 wt. %. The UV spectra of 2,2'-methylenebis[6-(2H-benzotriazole-2-yl)-4-(2-hydroxyethyl) phenol] and the copolyester were determined to calculate the benzotriazole content from the absorptivity coefficient ratio of the two substances.

The intrinsic viscosity was determined at a concentration of 10 g/l and at 30° C. using a mixted solvent of phenol and 1,1,2,2-tetrachloroethane (weight ratio=1:1).

Test Example 2

The copolyester synthesized in Example 20 was melted and formed into a film with a thickness of about 100 pm and used as the film of Test Example 2.

5 parts of the following UV absorber C or D was dry-blended with 95 parts of commercially available polethylene terephthalate resin not containing a UV absorber (tradename: MA-2103, product of Unitika, Ltd.) The obtained compositions were melted and formed into films with a thickness of about 100 μm in the same manner as in Test Example 2 (Comparisons C and D). When the composition containing UV absorber C was melted and formed into a film, the absorber was scattered as a yellowish white sublimate. The obtained films were then subjected to a 1200-hour accelerated weathering test using a Dew cycle sunshine Super Long-Life Weather Meter WEL-SUN-DC (product of Suga Test Instruments Co., Ltd., 18-minute rainfall every 120 minutes) and checked for the degree of yellowness (ΔYI) of the polyester resins. Table 2 shows the amounts of the components (parts=wt. parts) and the degree of yellowness after the accelerated test. It was revealed that the copolyester obtained in Example 20 has remarkably excellent weather resistance.

TABLE 2

| | Test Ex. 2 | Comp. C | Comp. D |
|---|---|---|---|
| Commercial PET resin | — | 95 parts | 95 parts |
| Copolyester of Ex. 20 | 100 parts | — | — |
| UV absorber C | — | 5 parts | — |
| Uv absorber D | — | — | 5 parts |
| Degree of yellowness (ΔYI) after 1200-hr test | 1.1 | 2.0 | 4.7 |

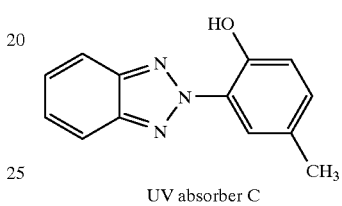

UV absorber C

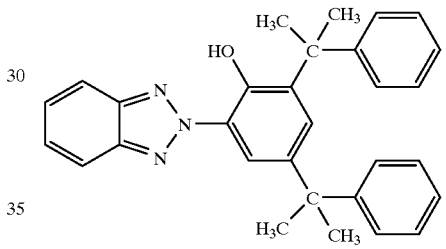

UV absorber D

EXAMPLE 21

25.02 g (0.1 mols) of diphenylmethane-4,4'-diisocyanate was added to 40 ml of 4-methylpentane-2-one, followed by vigorous stirring in a nitrogen atmosphere. To the obtained suspention were added a solution of 6.02 g (97 mmols) of ethylene glycol and 1.6 g (2.9 mmols) of 2,2'-methylenebis [6-(2H-benzotriazole-2-yl)-4-(3-hydroxypropyl)phenol] synthesized in Example 14 in 40 ml of dimethyl sulfoxide. The reaction mixture was heated to 115° C. with slow stirring to carry out a reaction for about 2 hours. After completion of the reaction, the reaction mixture was added to 200 ml of deionized water to precipitate a copolyurethane. The obtained white copolyurethane was dispersed in water, washed three times and dried in vacuum, giving an almost quantitive yield of objective copolyurethane as a white polymer (intrinsic viscosity 1.01 dl/g, mp 255° C.).

The UV absorber content in the copolyurethane was 5 wt. %. The UV spectra of 2,2'-methylenebis[6-(2H-benzotriazole-2-yl)-4-(3-hydroxypropyl)phenol] and the copolyurethane were determined to calculate the benzotriazole content from the absorptivity coefficient ratio of the two substances.

Test Example 3

100 parts of the copolyurethane synthesized in Example 21 was dissolved in 630 parts of dimethylformamide. The solution was applied to a circular quartz plate with a diameter of 300 mm using a spinner. The obtained coating was air-dried for 1 hour and then dried under reduced pressure at 60° C. for 12 hours to form on the plate a uniform thin film with a thickness of about 1 μm.

The plate was left to stand in deionized water at 70° C. for 40 hours, and the UV spectrum of the film was determined. Then, the absorbance (wave length 345 nm) of the film after the water resistance test was compared with that of the film before the test (Test Example 3). The retention of the absorbance was determined according to the following equation.

$$\text{Retention of absorbance}(\%) = \frac{\text{Absorbance of the film after the water resistance test}}{\text{Absorbance of the film before the water resistance test}} \times 100$$

For comparison, 95 parts of commercially available polyurethane resin not containing a UV absorber (tradename: Erastran C90A50, product of Takeda Badische Urethane Industries, Ltd.) was dissolved in 630 parts of dimethylformamide. To the solution was added 5 parts of UV absorber A (Comparison E) or 5 parts of UV absorber B (Comparison F). The obtained compositions were formed into films and subjected to the water resistance test in the same manner as in Test Example 3 to determine the change in absorbance (wave length 345 nm) with the lapse of time.

Table 3 shows the amounts of the components (parts=wt. parts) and the results of the determination.

UV absorbers A and B in the commercially available resin film dissolved out with the lapse of time, whereby the UW absorptivity was reduced by half in 40 hours. In contrast, the copolyurethane of Example 21 substantially did not change in absorptivity, and was found to have very high water resistance.

TABLE 3

|  | Test Ex. 3 | Comp. E | Comp. F |
| --- | --- | --- | --- |
| Commercial polyurethane resin | — | 95 parts | 95 parts |
| Copolyurethane of Ex. 21 | 100 parts | — | — |
| Dimethylformamide | 630 parts | 630 parts | 630 parts |
| UV absorber A | — | 5.0 parts | — |
| UV absorber B | — | — | 5.0 parts |
| Retention of absorbance | 99% | 41% | 50% |

EXAMPLE 22

In 60 ml of pyridine were dissolved 0.162 g (0.295 mmols) of 2,2'-methylenebis[6-(2H-benzotriazole-2-yl)-4-(3-hydroxypropyl)phenol] and 1.72 g (7.16 mmols) of bisphenol A. 2.08 g (6.87 mmols) of triphosgene was gradually added with stirring in a nitrogen stream. After further 1-hour stirring at room temperature, 250 ml of methanol was added to precipitate a polymer. The polymer was collected by filtration and dried under reduced pressure, giving 2.20 g of polycarbonate (copolycarbonate) as a white polymer, which contained 4.9 wt. % of 2,2'-methylenebis [6-(2H-benzotriazole-2-yl)-4-(3-hydroxypropyl) phenol].

The UV spectra of 2,2'-methylenebis[6-(2H-benzotriazole-2-yl)-4-(3-hydroxypropyl)phenol] and the copolycarbonate were determined to calculate the benzotriazole content from the absorptivity coefficient ratio of the two substances.

Test Examples 4 and 5

105 parts of the copolycarbonate synthesized in Example 19 or 22 was dissolved in 630 parts of 1,1,2,2-tetrachloroethane. The solution was applied to a circular quartz plate with a diameter of 300 mm using a spinner.

The obtained coating was air-dried for 1 hour and then dried under reduced pressure at 60° C. for 12 hours to form on the plate a uniform thin film with a thickness of about 1 μm. The plate was left to stand in deionized water at 70° C. for 40 hours. The retention of absorbance (wave length 345 nm) was determined in the same manner as in Test Example 3. The results are shown in Table 4.

For comparison, 100 parts of commercially available polycarbonate resin not containing a UV absorber (tradename: E-2000, product of Mitsubishi Gas Chemical, Co., Inc.) was dissolved in 630 parts of 1,1,2,2-tetrachloroethane. To the solution was added 5 parts of UV absorber A (Comparison G) or 5 parts of UV absorber B (Comparison H). The obtained compositions were formed into films and subjected to the water resistance test in the same manner as in Test Examples 4 and 5 to determine the retention of absorbance. Table 4 shows the amounts of the components (parts=wt. parts) and the results of the determination. Absorbers A and B in the commercially available resin films dissolved out into the warm water with the lapse of time. After 40 hours, the films of the commercially available resins had substancially no UV absorptivity. In contrast, the copolycarbonates of Examples 19 and 22 substantially did not change in absorptivity, and were found to have very high water resistance.

TABLE 4

|  | Test Ex. 4 | Test Ex. 5 | Comp. E | Comp. F |
| --- | --- | --- | --- | --- |
| Commercial polycarbonate resin | — | — | 100 parts | 100 parts |
| Copolycarbonate of Ex. 19 | 100 parts | — | — | — |
| Copolycarbonate of Ex. 22 | — | 105 parts | — | — |
| 1, 1, 2, 2-Tetrachloroethane | 630 parts | 630 parts | 630 parts | 630 parts |
| UV absorber A | — | — | 5.0 parts | — |
| UV absorber B | — | — | — | 5.0 parts |
| Retention of absorbance | 98% | 99% | 12% | 23% |

EXAMPLE 23

Mixed together were 90 g of tetramethylene glycol with a number average molecular weight of 2000, 10 g of 2,2'-methylenebis[6-(2H-benzotriazole-2-yl)-4-(2-hydroxyethyl)phenol] and 25 g of 4,4'-diphenylmethane-diisocyanate. The mixture was stirred in a nitrogen atmosphere at 85° C. for 3 hours, giving a quantitive yield of polyurethane oligomer having isocyanate groups at both ends. To the reaction mixture was added 120 g of dry dimethylacetoamide, followed by stirring at room temperature to obtain a dimethylacetoamide solution of oligomer. The solution was vigorously stirred, and an amine solution previously prepared by dissolving 2.4 g of ethylenediamine and 0.6 g of diethylamine in 120 g of dimethylacetoamide was added dropwise. The mixture was stirred for 3 hours, giving a dimethylacetoamide solution of modified polyurethaneurea with a viscosity of 930 poise (30° C.). The solution was fed into a dry-spinning machine with a jacket temperature of 220° C. to prepare an elastic fiber with a fineness of 40 denier. The elastic fiber had breaking strength of 67.5 g/d and breaking extension of 560%.

The breaking strength and breaking extension were determined by the following methods.

A test thread was set on an Instron type tensile tester (tradename: Autograph DCS-2000, product of Shimadzu Corp.) which had been set at a measuring temperature of 20° C. and a grip distance of 50 mm. The test thread was stretched at a deformation rate of 1000%/mmn until breaking to determine the stress (strength) and extension at the time of breaking. The breaking strength was expressed in grams per denier of the original thread, and the breaking extension in elongation (%) relative to the initial length.

EXAMPLE 24

A modified polyurethaneurea elastic fiber with a fineness of 40 denier was prepared by following the procedure of Example 23 and using 90 g of tetramethylene glycol with a number average molecular weight of 2000, 10 g of 2,2'-methylenebis[6-(5-chloro-2H-benzotriazole-2-yl)-4-(2-hydroxyethyl)phenol] synthesized in Example 13 and 25 g of 4,4'-diphenylmethane diisocyanate. The obtained elastic fiber was checked for the properties in the same manner as in Example 23 and found to have breaking strength of 68.2 g/d and breaking extension of 566%.

EXAMPLE 25

A modified polyurethaneurea elastic fiber with a fineness of 40 denier was prepared by following the procedure of Example 23 and using 90 g of tetramethylene glycol with a number average molecular weight of 2000, 10 g of 2,2'-methylenebis[6-(2H-benzotriazole-2-yl)- 4-(3-hydroxypropyl)phenol] and 25 g of 4,4'-diphenylmethane-diisocyanate. The obtained elastic fiber was checked for the properties in the same manner as in Example 23 and found to have breaking strength of 67.2 g/d and breaking extension of 562%.

EXAMPLE 26

A modified polyurethaneurea elastic fiber with a fineness of 40 denier was prepared by following the procedure of Example 23 and using 90 g of tetramethylene glycol with a number average molecular weight of 2000, 10 g of 2,2'-methylenebis[6-(2H-benzotriazole-2-yl)-4-(4-hydroxybutyl)phenol] and 25 g of 4,4'-diphenylmethane diisocyanate. The obtained elastic fiber was checked for the properties in the same manner as in Example 23 and found to have breaking strength of 65.9 g/d and breaking extension of 562%.

Comparative Example 1

Mixed together were 100 g of tetramethylene glycol with a number average molecular weight of 2000 and 25 g of 4,4'-diphenylmethane diisocyanate. The mixture was stirred in a nitrogen atmosphere at 85° C. for 3 hours, giving a polyurethane oligomer having isocyanate groups at both ends. To the reaction mixture was added 120 g of dry dimethylacetoamide, followed by stirring at room temperature to prepare a dimethylacetoamide solution of oligomer. The solution was vigorously stirred, and an amine solution previously prepared by dissolving 1.9 g of ethylenediamine and 0.5 g of diethylamine in 120 g of diethylacetoamide was added dropwise. The mixture was stirred for 3 hours, giving a dimethylacetoamide solution of polyurethaneurea with a viscosity of 780 poise (30° C.). 10 g of UV absorber B was dissolved in the solution to prepare a composition for spinning. The composition was fed into a dry-spinning machine with a jacket temperature of 220° C. to prepare an elastic fiber with a fineness of 40 denier. The obtained elastic fiber was checked for the properties in the same manner as in Example 23 and found to have breaking strength of 58.7 g/d and breaking extension of 472%.

Test Examples 6 to 9

The polyurethaneurea elastic fibers synthesized in Examples 23, 24, 25 and 26were subjected to a 500-hour accelerated weathering test using a Dew cycle sunshine weatherometer WEL-SUN-DC (product of Suga Shikenki Co., Ltd., 18-minute rainfall every 120 minutes). The breaking strength of the fibers was determined in the same manner as in Example 23 and compared with that of the fibers before the weathering test. The retention of the breaking strength was calculated according to the following equation (Test Examples 6, 7, 8 and 9).

$$\text{Retention of breaking strength (\%)} = \frac{\text{Breaking strength after the accelerated weathering test}}{\text{Breaking strength before the accelerated weathering test}} \times 100$$

For comparison, the polyurethaneurea elastic fiber synthesized in Comparative Example 1 which contained commercially available UV absorber B was subjected to the accelerated weathering test to determine the breaking strength and calculate the retention thereof in the same manner as in Test Example 6 (Comparison I). The results are shown in Table 5.

TABLE 5

|  | Breaking strength after weathering test | Retention of breaking strength | Appearance |
| --- | --- | --- | --- |
| Test Ex. 6 | 63.5 g/d | 94% | No change |
| Test Ex. 7 | 66.8 g/d | 98% | No change |
| Test Ex. 8 | 62.5 g/d | 93% | No change |
| Test Ex. 9 | 61.3 g/d | 93% | No change |
| Comparison I | 14.7 g/d | 25% | Yellowness |

It was revealed that the polyurethaneurea elastic fiber of Comparative Example 1 yellowed and had a breaking strength retention as low as 25%. In contrast, the modified polyurethaneurea elastic fibers of Examples 23, 24, 25 and 26 had substantially no change in appearance and breaking strength after the accelerated weathering test.

We claim:

1. A bisbenzotriazolylphenol compound represented by the formula

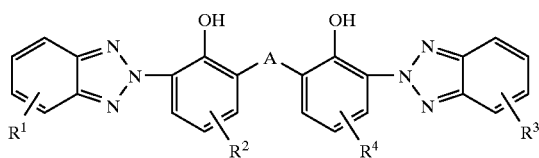

wherein A is a direct bond or represents a $C_{1-6}$ alkylene group, a —C(CH$_3$)$_2$— group, a —C(C$_2$H$_5$)(CH$_3$)— group, a —O— group or a —NH— group, $R^1$ and $R^2$ are the same or different and each represent a hydrogen atom, a $C_{1-4}$ alkyl group, an aryl group, a $C_{1-4}$ alkoxy group or a halogen atom, and $R^2$ and $R^4$ are the same or different and each represent a hydroxyl group or a $C_{1-12}$ straight- or branched-chain hydroxyalkyl group.

2. A bisbenzotriazolylphenol compound according to claim 1 wherein $R^2$ and $R^4$ are both $C_{1-12}$ straight- or branched-chain hydroxyalkyl groups.

3. A bisbenzotriazolylphenol compound according to claim 1 wherein A is a methylene group.

4. A copolymer comprising as a copolymerization component 0.01 to 70 wt. % of a bisbenzotriazolylphenol compound according to claim 1.

5. A copolymer according to claim 4 which is a copolycarbonate, a copolyester, a copolyurethane or a copolyurethaneurea.

6. A bisbenzotriazolylphenol compound according to claim 2 wherein A is a methylene group.

* * * * *

UNITED STATES PATENT AND TRADEMARK OFFICE
CERTIFICATE OF CORRECTION

PATENT NO. : 5,922,882

DATED : July 13, 1999

INVENTOR(S): Koji Mori, Emiko Daimon, Koji Ishida, Shinji Nakano, Takashi Ogawa, Kazuhiro Kawano and Mitsuo Akada It is certified that error appears in the above-identified patent and that said Letters Patent is hereby corrected as shown below:

On the title page: Item [87] PCT Publication Date, please correct

"February 10, 1997" to --October 2, 1997--.

Signed and Sealed this

Eighth Day of February, 2000

*Attest:*

*Attesting Officer*

Q. TODD DICKINSON

*Commissioner of Patents and Trademarks*